United States Patent [19]

Shukunobe et al.

[11] Patent Number: 4,983,361
[45] Date of Patent: Jan. 8, 1991

[54] REACTOR PROVIDED WITH FLUIDIZED CHAMBER

[75] Inventors: Yukitaka Shukunobe, Kawagoe; Tetsuo Nakamura, Iruma; Koji Aono, Tokyo; Ryoichi Doki, Sayama; Mamoru Kuwazuru, Kawagoe; Kouzou Shimoda, Tokyo; Tomoe Yoshida, Tokorozawa, all of Japan

[73] Assignee: R&D Association for Bioreactor System, Tokyo, Japan

[21] Appl. No.: 287,306

[22] Filed: Dec. 21, 1988

[30] Foreign Application Priority Data

Dec. 28, 1987 [JP] Japan ................... 62-336364

[51] Int. Cl.$^5$ .............................. B01J 8/02; B01J 8/20
[52] U.S. Cl. .................................... 422/145; 422/219; 422/233; 422/292; 134/166 R; 134/177
[58] Field of Search ............... 422/219, 232, 233, 140, 422/143, 145, 292; 134/25.1, 166 R, 169 R, 177, 186

[56] References Cited

U.S. PATENT DOCUMENTS 4,670,140 6/1987 Aivasidis et al. ............... 422/193 X

FOREIGN PATENT DOCUMENTS 61-12280 1/1986 Japan .

Primary Examiner—Robert J. Warden
Assistant Examiner—Jeffrey R. Snay
Attorney, Agent, or Firm—Griffin Branigan & Butler

[57] ABSTRACT

A reactor provided with a fluidized chamber is characterized in that the fluidized chamber is connected with a column chamber, an inner tube movable in the fluidized chamber is provided, the inner tube is arranged to be brought into contact with the column chamber through the fluidized chamber and nets for preventing outflow of immobilized biocatalyst, gel, immobilized carrier or the like are provided at the head opening of the inner tube and the column chamber, respectively.

7 Claims, 3 Drawing Sheets

REACTOR PROVIDED WITH FLUIDIZED CHAMBER

BACKGROUND OF THE INVENTION

The present invention relates to an apparatus for reducing difficulties of washing and disinfecting immobilized enzymes or immobilized myceliums (hereinafter referred to as immobilized biocatalyst) and absorption of useful materials to gel, immobilized carrier or the like in a reactor which is used when using a raw material including materials to which protein or the like is easily attached.

Heretofore, the art of production by the immobilized biocatalyst has been extremely innovated and there are many reactors such as packed layer type, fluidized bed type, stirred tank type and membrane type reactors applied to the above-mentioned field. In regard to the art of washing and disinfecting the immobilized biocatalyst in the reactors, there is background art disclosed in the Japanese Patent Publication No. 33873/87. In the above invention, a reactor is connected to an apparatus for washing and disinfecting the immobilized biocatalyst through a closed circuit so as to enable a cycle carriage of the immobilized biocatalyst dispersed in water.

In the invention of said Japanese Patent Publication No. 33873/87, the apparatus for washing-disinfecting and the reactor are disposed separately. Therefore, the apparatus for washing-disinfecting cannot be driven when the reactor is in used, resulting in bad efficiency. Further, there needs to be another separate space for providing the apparatus for washing-disinfecting, resulting in uneconomical increase of cost. Further, even with the closed circuit, the reactor and the apparatus for washing-disinfecting are connected to each other through pipes and valves, and therefore it is possible that the immobilized biocatalyst is contaminated by the above connecting means.

Further, in the washing-disinfecting operation using the prior fluidized chamber, there needs to be driving systems for stirring or washing, because the column chamber and the immobilized biocatalyst are washed separately.

SUMMARY OF THE INVENTION

Accordingly, the object of the present invention is to provide an apparatus for reducing difficulties of washing-disinfecting of immobilized biocatalyst and absorption of useful materials to gel, immobilized carrier or the like without providing another separate space for a means for washing-disinfecting and driving systems for stirring or washing. According to the present invention, so as to attain the above-mentioned object, there is provided a reactor provided with a fluidized chamber characterized in that the fluidized chamber is connected with a column chamber having a net (or screen or the like) for preventing outflow of immobilized biocatalyst, gel, immobilized carrier or the like therein, an inner tube having a net (or screen or the like) for preventing outflow of immobilized biocatalyst, gel, immobilized carrier or the like and at its head opening extends through the fluidized chamber to the column chamber so as to have a contact with the column chamber and the inner tube is arranged to be movable in the fluidized chamber.

In regard to the operation of the reactor provided with the fluidized chamber according to the present invention, an embodiment of elution, washing and disinfecting will be explained based on FIG. 1. A solution containing substrate is introduced into an inner tube 12 from an inlet 12A and descends to a packed chamber 17 through an upper net 14 for preventing outflow so as to react with the immobilized biocatalyst packed in the packed chamber 17. The reacted solution flows to a next step through a lower net 15 for preventing outflow. When washing and disinfecting the immobilized biocatalyst is conducted, because of the large pressure loss caused by attachment of protein or the like to the immobilized biocatalyst, the inner tube 12 is taken up so as to bring an outer surface of a head opening 13 into contact with an inner surface of an upper surface of funnel portion 4. Washing liquid is introduced into the reactor at high pressure through a funnel tube 9 and discharged from the head opening 13 through the inner tube 12. With this, the immobilized biocatalyst can be moved freely from the upper net 14 for preventing outflow of the upper funnel portion 4 of the fluidized chamber 2 to the lower net 15 for preventing outflow disposed at lower portion of a column chamber 3 and therefore a vortex flow of the washing liquid is generated mainly in the fluidized chamber 2 and the immobilized biocatalyst is stirred and washed by said vortex flow. After washing, the immobilized biocatalyst is sterilized by a surface active agent such as quaternary ammonium salt and said sterilizing operation is also conducted by introducing the disinfection liquid into the reactor at high pressure through the funnel tube 9 and discharging the liquid from the head opening 13 through the inner tube 12 by the same way as the above-mentioned washing operation. Thereafter when stopping supply of the disinfection solvent, the washed and sterilized immobilized biocatalyst is fallen to the column chamber 3. Thereafter, the outer periphery of the head opening 13 of the inner tube 12 is brought into contact with an inner surface 3A of the column chamber 3. The remaining liquid in the fluidized chamber is discharged from an outlet 10 for the washing liquid or the like disposed at a higher position than the head opening 13.

The reactor provided with the fluidized chamber according to the present invention has following advantages:

In the reactor provided with the fluidized chamber according to the present invention, because the means for washing and disinfecting the immobilized biocatalyst is integrally provided in the reactor, there is no need to provide another separate space for the means for washing and disinfecting the immobilized biocatalyst, therefore it becomes very effective and economical.

Further, in the reactor provided with the fluidized chamber according to the present invention, because the pipe and the valve assembly for washing and disinfecting is not arranged out of the reactor, the immobilized biocatalyst is not contaminated by those assemblies.

Further, there is no need to provide the driving systems for stirring and washing, because the washing liquid and the disinfection liquid are introduced into the reactor at high pressure.

Further, in the reactor provided with fluidized chamber according to the present invention, the absorption of the useful material to gel, immobilized carrier or the like can be conducted.

BRIEF DESCRIPTION OF THE DRAWINGS

The above and other objections of the invention will be seen by reference to the description taken in connection with the accompanying drawings, in which.

DESCRIPTION OF THE INVENTION

Figure 1:
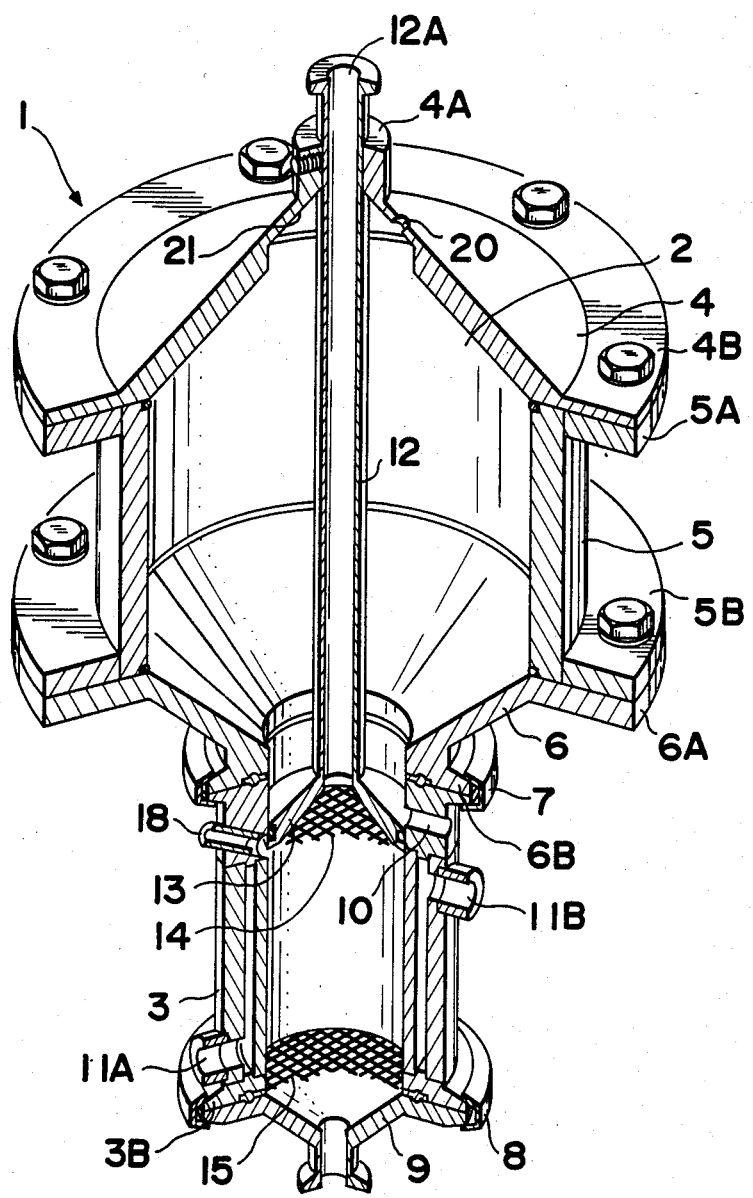
FIG. 1 is a perspective view including partial section view, which shows one embodiment of the reactor provided with the fluidized chamber according to the present invention.

Referring to the drawings, as shown in FIG. 1, reference numeral 1 shows a reactor wherein a hollow column chamber 3 is connected with a down portion of a hollow fluidized chamber 2. The fluidized chamber 2 is formed by a central cylinder portion 5, an upper funnel portion 4 and lower funnel portion 6. The lower flange 4B of the upper funnel portion 4 and the upper flange 5A of the cylinder portion 5, and the lower flange 5B of the cylinder portion 5 and the upper flange 6A of the lower funnel portion 6 are bolted, respectively.

There is provided a flange 6B at the lower portion of the lower funnel portion 6, which flange 6B is connected with an upper flange of the column chamber 3 through a clamp coupling 7 to form a juncture between the two chambers. The lower flange 3B of the column chamber 3 is connected with the upper flange of the funnel 9 through a clamp coupling 8. There is provided an outlet 10 for washing liquid or the like at the upper portion of the column 3 and a jacket 11 is provided about the outer periphery of the lower portion of the column chamber 3. The reference numerals 11A and 11B show an inlet and an outlet for cooling water filled in the jacket 11.

Figure 2:
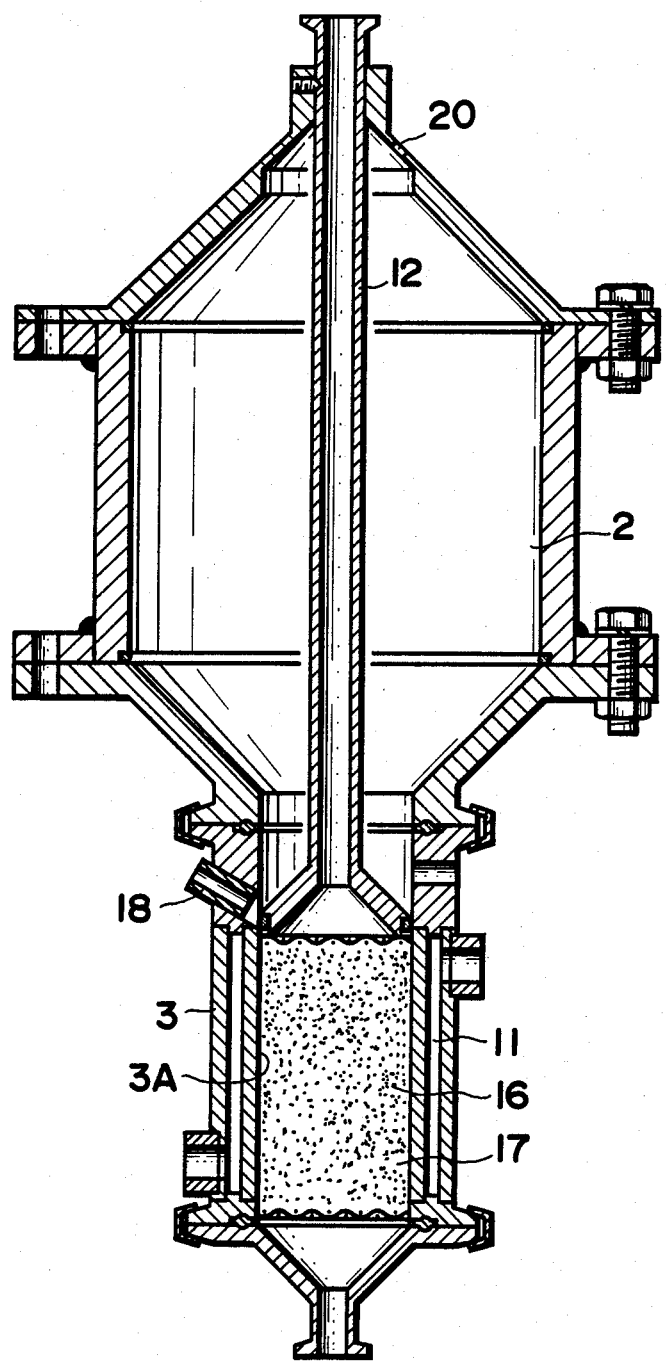
FIG. 2 is a sectional view of the reactor provided with the fluidized chamber described in FIG. 1.

The reference numeral 12 shows an inner tube, which extends through an inlet 4A for the inner tube and has a head portion with a funnel head opening 13 at one end portion thereof. A net or screen 14 for providing outflow is provided on the outer surface of the head opening 13. The outer periphery of the head opening 13 is adjusted to contact with an inner surface or wall 3A (see FIG. 2) of the column chamber 3. The inner tube 12 can be moved up and down. Therefore, when washing and disinfecting an immobilized biocatalyst, the inner tube 12 is moved upwardly so as to bring the outer surface of the head portion with head opening 13 into contact with the upper inner surface of the upper funnel portion 4. The reference numeral 20 shows an air vent and the reference numeral 21 shows a portion to which the funnel head opening 13 is fitted.

Figure 3:
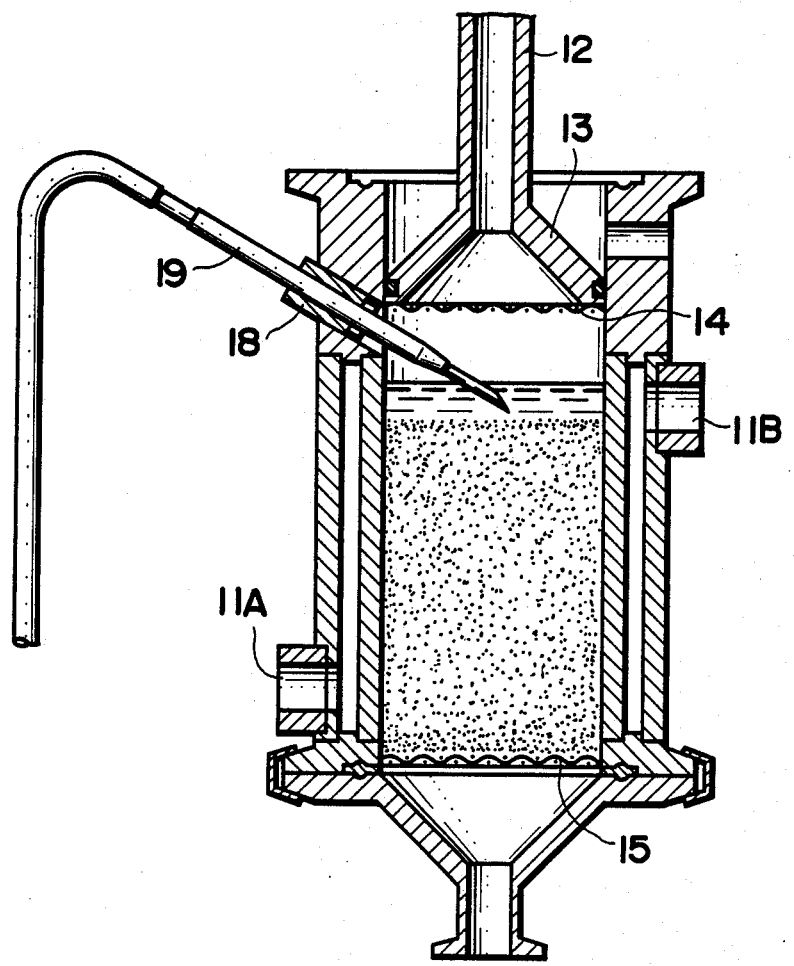
FIG. 3 is a detailed explanational view showing the column chamber.

Another net or screen 15 for preventing outflow is provided at the lower end portion of the column chamber 3. The reactive solids, e.g. immobilized biocatalyst, 16 disposed in is packed chamber 17 and contained therein by the upper net 14 for preventing outflow of the solids, the inner wall or surface 3A and lower screen or the net 15 for preventing outflow of the solids. Referring to FIG. 3, the reference numeral 18 shows an output port for taking out a sample of the immobilized biocatalyst and the reference numeral 19 shows a sample tube which can be freely inserted into and out of the output port 18. A pinchcock (not shown) is provided at the end of thereof. The liquid filled in the packed chamber 17 and the immobilized biocatalyst can be freely taken out by inserting the sample tube 19 into and out of the output port 18 for the sample. Since the inner pressure in the column chamber is higher than the atmospher pressure, there is no need to use a particular technical means for taking out the liquid and the immobilized biocatalyst. Thus the situation of washing-disinfecting of the immobilized biocatalyst and the elution capacity can be estimated by examining the sample taken out of the output port 18.

Further the reactor according to the present invention is not limited to a downward flow type packed layer reactor and can be adapted to a upward flow type packed layer reactor and also can be adapted to a fluidized bed reactor.

Further, while maintaining a situation such that the inner tube 12 is taken out so as to bring the outer surface of the head opening 13 into contact with the upper inner surface of the upper funnel portion 4, a useful material can be applied through the funnel 9 and be absorbed by gel or immobilized carrier filled between the net or screen 14 for preventing outflow and the net or screen 15 for preventing outflow.

While the invention has been particularly shown and described with reference to preferred embodiment thereof, it will be understood by those skilled in the art that the foregoing and other changes in form and details can be make therein without departing from the sprit and scope of the invention.

What is claimed is:

1. A reactor for containing a bed of reactive solids and having a fluidized chamber associated therewith for periodic fluid treatment of the reactive solids, comprising:
   (1) a generally vertically-disposed column chamber for containing the reactive solids;
   (2) a first screen disposed near a lower end of the column chamber for supporting the reactive solids;
   (3) a fluidized chamber of greater volume than the volume of said column chamber and being disposed generally above and in fluid communication with said column chamber at a fluid communicating juncture therebetween;
   (4) a straight hollow interior inner tube extending from an upper portion of the fluidized chamber to near said juncture and terminating in a head portion;
   (5) a head opening in said head portion in fluid communication with the hollow interior of said inner tube;
   (6) a second screen disposed over said head opening so that the reactive solids are containable in said column chamber between vertical inner walls of the column chamber and said first and second screens;
   (7) means for allowing movement of said inner tube vertically upwardly until said head portion is near a top portion of said fluidized chamber; and
   (8) means for introducing a washing fluid or the like into a bottom portion of the column chamber such as to wash reactive solids moved to the fluidized chamber;
   and wherein said fluidized chamber has a configuration such that when said washing fluid is discontinued, reactive solids in said fluidized chamber settle into said column chamber.

2. A reactor according to claim 1, wherein an outlet for washing fluid or the like is disposed near the juncture of the fluidized chamber and the column chamber.

3. A reactor according to claim 1 wherein the means for introducing a washing fluid or the like into a bottom portion of the column chamber is such as to move reactive solids disposed therein from said column chamber and fluidize the solids in the fluidized chamber, and the washing fluid is passable out of the fluidized chamber through said second screen over said head opening and through said inner tube when said head portion is disposed near the top portion of the fluidized chamber and wherein when the reactive solids settle into said column chamber, the solids are again retainable therein by movement of the said head portion to said juncture.

4. A reactor according to claim 1, wherein the shape of the head opening of the head portion of the inner tube is funnel or cylindrical.

5. A reactor according to claim 4, wherein the head opening is contactable with the juncture, said juncture being formed by the walls of the column chamber.

6. A reactor according to claim 5, wherein a fit portion fitting to the head opening of the inner tube is provided in a surface of the fluidized chamber opposite to a surface thereof connected with the column chamber.

7. A reactor according to any one of claims 1 and 3 to 6, wherein a jacket is provided around an outer periphery of the column chamber.

* * * * *